United States Patent
Ashton et al.

(10) Patent No.: US 11,661,428 B1
(45) Date of Patent: May 30, 2023

(54) NONLINEAR OPTICAL CHROMOPHORES, NONLINEAR OPTICAL MATERIALS CONTAINING THE SAME, AND USES THEREOF IN OPTICAL DEVICES

(71) Applicant: LIGHTWAVE LOGIC, INC., Englewood, CO (US)

(72) Inventors: Andrew Ashton, Newark, DE (US); Barry Johnson, Newark, DE (US)

(73) Assignee: LIGHTWAVE LOGIC, INC., Englewood, CO (US)

( * ) Notice: Subject to any disclaimer, the term of this patent is extended or adjusted under 35 U.S.C. 154(b) by 0 days.

(21) Appl. No.: 16/150,684

(22) Filed: Oct. 3, 2018

Related U.S. Application Data

(60) Provisional application No. 62/567,430, filed on Oct. 3, 2017.

(51) Int. Cl.
| | |
|---|---|
| *C07D 307/30* | (2006.01) |
| *C07D 307/54* | (2006.01) |
| *G02F 1/361* | (2006.01) |
| *B05D 3/14* | (2006.01) |
| *C07D 495/04* | (2006.01) |
| *C07D 307/52* | (2006.01) |

(52) U.S. Cl.
CPC ......... *C07D 495/04* (2013.01); *C07D 307/52* (2013.01); *G02F 1/3614* (2013.01); *G02F 1/3617* (2013.01)

(58) Field of Classification Search
CPC .. C07D 307/30; C07D 307/52; C07D 307/54; C07D 491/048; C07D 495/04; G02F 1/361; G02F 1/3614; G02F 1/3617; C08G 73/02; C08G 75/06
See application file for complete search history.

(56) References Cited

U.S. PATENT DOCUMENTS

2009/0137772 A1* 5/2009 Huang .................. G02F 1/3611
549/474

OTHER PUBLICATIONS

Scott R. Hammond, Jessica Sinness, Sara Dubbury, Kimberly A. Firestone, Jason B. Benedict,,Zdzislaw Wawrzak.bOlivier Clot, Philip J. Reid and Larry R. Dalton,Molecular engineering of nanoscale order in organic electro-optic glasses, J. Mater. Chem., 2012, 22, 6752-6764. (Year: 2012).*

* cited by examiner

*Primary Examiner* — Bijan Ahvazi
(74) *Attorney, Agent, or Firm* — Flaster Greenberg, P.C.

(57) ABSTRACT

Nonlinear optical chromophores having thiophene-containing bridging groups between the electron-donating and electron-accepting ends of the chromophore are disclosed, including bridging groups which contain cyclic moieties in combination with conjugated double bonds between the electron-donating and electron-accepting ends of the chromophore.

1 Claim, No Drawings

NONLINEAR OPTICAL CHROMOPHORES, NONLINEAR OPTICAL MATERIALS CONTAINING THE SAME, AND USES THEREOF IN OPTICAL DEVICES

CROSS-REFERENCE TO RELATED APPLICATIONS

This application claims the benefit of U.S. Provisional Patent Application No. 62/567,430, filed Oct. 3, 2017, the entire contents of which are hereby incorporated by reference herein.

BACKGROUND OF THE INVENTION

Polymeric electro-optic (EO) materials have demonstrated enormous potential for core application in a broad range of systems and devices, including phased array radar, satellite and fiber telecommunications, cable television (CATV), optical gyroscopes for application in aerial and missile guidance, electronic counter measure systems (ECM) systems, backplane interconnects for high-speed computation, ultrafast analog-to-digital conversion, land mine detection, radio frequency photonics, spatial light modulation and all-optical (light-switching-light) signal processing.

Nonlinear optical ("NLO") materials are capable of varying their first-, second-, third- and higher-order polarizabilities in the presence of an externally applied electric field or incident light (two-photon absorption). In telecommunication applications, the second-order polarizability (hyperpolarizability or $\beta$) and third-order polarizability (second-order hyperpolarizability or $\gamma$) are currently of great interest. The hyperpolarizability is related to the change of a NLO material's refractive index in response to application of an electric field. The second-order hyperpolarizability is related to the change of refractive index in response to photonic absorbance and thus is relevant to all-optical signal processing. The third-order polarizability relates to the change of refractive index in response to an intense light field. A more complete discussion of nonlinear optical materials may be found in D. S. Chemla and J. Zyss, Nonlinear optical properties of organic molecules and crystals, Academic Press, 1987 and K.-S. Lee, Polymers for Photonics Applications I, Springer 2002, the entire contents of which are hereby incorporated by reference.

Many NLO molecules (chromophores) have been synthesized that exhibit high molecular electro-optic properties. The product of the molecular dipole moment ($\mu$) and hyperpolarizability ($\beta$) is often used as a measure of molecular electro-optic performance due to the dipole's involvement in material processing. One chromophore originally evaluated for its extraordinary NLO properties by Bell Labs the 1960s, Disperse Red (DR), exhibits an electro-optic coefficient $\mu\beta \sim 580 \times 10^{-48}$ esu. Current molecular designs, including FTC, CLD and GLD, exhibit $\mu\beta$ values in excess of $10,000 \times 10^{-48}$ esu. See Dalton et al., "New Class of High Hyperpolarizability Organic Chromophores and Process for Synthesizing the Same", WO 00/09613, the entire contents of which are hereby incorporated by reference.

Nevertheless extreme difficulties have been encountered translating microscopic molecular hyperpolarizabilities ($\beta$) into macroscopic material hyperpolarizabilities ($\chi^{(2)}$). Molecular subcomponents (chromophores) must be integrated into NLO materials that exhibit: (i) a high degree of macroscopic nonlinearity; and, (ii) sufficient temporal, thermal, chemical and photochemical stability. Simultaneous solution of these dual issues is regarded as the final impediment in the broad commercialization of EO polymers in numerous government and commercial devices and systems.

The production of high material hyperpolarizabilities ($\chi^{(2)}$) is limited by the poor social character of NLO chromophores. Commercially viable materials must incorporate chromophores with the requisite molecular moment statistically oriented along a single material axis. In order to achieve such an organization, the charge transfer (dipolar) character of NLO chromophores is commonly exploited through the application of an external electric field during material processing which creates a localized lower-energy condition favoring noncentrosymmetric order. Unfortunately, at even moderate chromophore densities, molecules form multi-molecular dipolarly-bound (centrosymmetric) aggregates that cannot be dismantled via realistic field energies. As a result, NLO material performance tends to decrease dramatically after approximately 20-30% weight loading.

The synthesis and development of chromophores that exhibit excellent electro-optical properties and excellent stability is thus an important goal in the field, and providing such chromophores is thus highly desirable.

BRIEF SUMMARY OF THE INVENTION

The present invention is directed, in general, to nonlinear optical chromophores. In particular, in various embodiments, the present invention relates to nonlinear optical chromophores having thiophene-containing bridging groups between the electron-donating and electron-accepting ends of the chromophore. In various embodiments, the present invention relates to nonlinear optical chromophores having bridging groups which contain cyclic moieties in combination with conjugated double bonds between the electron-donating and electron-accepting ends of the chromophore.

Various embodiments of the present invention thus provide nonlinear optical chromophores with significantly improved optical properties and nonlinear optical chromophores with significantly improved stability.

One embodiment of the present invention includes nonlinear optical chromophores of the general formula (I):

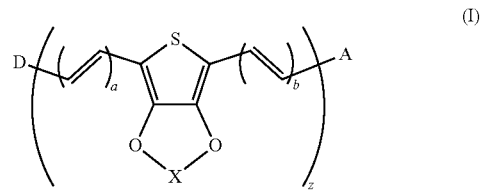

wherein D represents a moiety comprising an electron-donating group; wherein A represents a moiety comprising an electron-accepting group; wherein X represents a substituted or unsubstituted, branched or unbranched $C_2$-$C_4$ diyl moiety; wherein each a and b independently represents an integer of 0 to 3; and z represents an integer of 1 to 3.

In various preferred embodiments of the present invention, the nonlinear optical chromophores have the general formula (I');

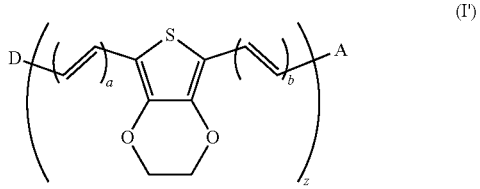

(I')

wherein A, D, a and b are defined as above.

Various particularly preferred embodiments of the present invention include a nonlinear optical chromophore of the general formula (I''):

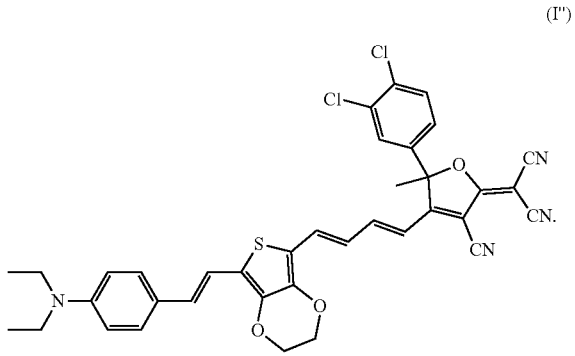

(I'')

Another embodiment of the present invention includes nonlinear optical chromophores of the general formula (II):

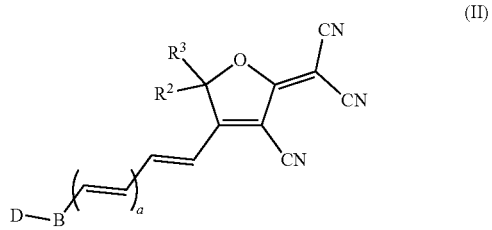

(II)

wherein D represents a moiety comprising an electron-donating group; wherein B comprises at least one bivalent ring; wherein $R^2$ and $R^3$ each independently represents a moiety selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocyclic, substituted or unsubstituted heterocyclic, substituted or unsubstituted cyclohexyl, and $(CH_2)_n$—O—$(CH_2)_n$ where n is 1-10; and wherein a represents an integer of 1 or 2.

Nonlinear optical chromophores and compositions containing one or more such chromophores according to the present invention (referred to herein collectively as "nonlinear optical chromophores according to the present invention") surprisingly provide a significant improvement over existing chromophore architectures by exhibiting significantly greater electro-optic properties and also possessing a high degree of stability.

Another embodiment of the present invention includes nonlinear optical materials which comprise a nonlinear optical chromophore according to an embodiment of the present invention or mixtures in accordance with various embodiments of the present invention incorporated within a matrix material. Suitable matrix materials can include various polymers, solutions, glass and others. Suitable methods for incorporating a nonlinear optical chromophores according to the present invention into a polymer matrix material include: combining the chromophore with the polymer; electric field poling of the chromophore/polymer mixture to acentrically align chromophores; followed by crosslinking, curing, and/or hardening the chromophore-containing polymer. In various preferred embodiments, the chromophore can be physically incorporated into a polymer to provide a composite. In various embodiments, the chromophore can be covalently incorporated into the polymer by, for example, attachment as a side chain or crosslinking. In various embodiments, the chromophore can be crosslinked to the polymer in more than one position, for example, a double-ended crosslinked chromophore.

Yet another embodiment of the present invention includes electro-optic devices which comprise a nonlinear optical material in accordance with various other embodiments of the present invention.

Other aspects, features and advantages will be apparent from the following disclosure, including the detailed description, preferred embodiments, and the appended claims.

DETAILED DESCRIPTION OF THE INVENTION

As used herein, the singular terms "a" and "the" are synonymous and used interchangeably with "one or more" and "at least one," unless the language and/or context clearly indicates otherwise. Accordingly, for example, reference to "a polymer" or "the polymer" herein or in the appended claims can refer to a single polymer or more than one polymer. Additionally, all numerical values, unless otherwise specifically noted, are understood to be modified by the word "about."

As used herein, the term "nonlinear optic chromophore" (NLOC) refers to molecules or portions of a molecule that create a nonlinear optic effect when irradiated with light. The chromophores are any molecular unit whose interaction with light gives rise to the nonlinear optical effect. The desired effect may occur at resonant or nonresonant wavelengths. The activity of a specific chromophore in a nonlinear optic material is stated as its hyper-polarizability, which is directly related to the molecular dipole moment of the chromophore. The inventive stabilized radical NLO chromophores of the present invention are useful structures for the production of NLO effects.

The first-order hyperpolarizability ($\beta$) is one of the most common and useful NLO properties. Higher-order hyperpolarizabilities are useful in other applications such as all-optical (light-switching-light) applications. To determine if a material, such as a compound or polymer, includes a nonlinear optic chromophore with first-order hyperpolar character, the following test may be performed. First, the material in the form of a thin film is placed in an electric field to align the dipoles. This may be performed by sandwiching a film of the material between electrodes, such as indium tin oxide (ITO) substrates, gold films, or silver films, for example.

To generate a poling electric field, an electric potential is then applied to the electrodes while the material is heated to near its glass transition ($T_g$) temperature. After a suitable period of time, the temperature is gradually lowered while maintaining the poling electric field. Alternatively, the material can be poled by corona poling method, where an electrically charged needle at a suitable distance from the material film provides the poling electric field. In either instance, the dipoles in the material tend to align with the field.

The nonlinear optical property of the poled material is then tested as follows. Polarized light, often from a laser, is passed through the poled material, then through a polarizing filter, and to a light intensity detector. If the intensity of light received at the detector changes as the electric potential applied to the electrodes is varied, the material incorporates a nonlinear optic chromophore and has an electro-optically variable refractive index. A more detailed discussion of techniques to measure the electro-optic constants of a poled film that incorporates nonlinear optic chromophores may be found in Chia-Chi Teng, Measuring Electro-Optic Constants of a Poled Film, in Nonlinear Optics of Organic Molecules and Polymers, Chp. 7, 447-49 (Hari Singh Nalwa & Seizo Miyata eds., 1997), incorporated by reference in its entirety, except that in the event of any inconsistent disclosure or definition from the present application, the disclosure or definition herein shall be deemed to prevail.

The relationship between the change in applied electric potential versus the change in the refractive index of the material may be represented as its EO coefficient $r_{33}$. This effect is commonly referred to as an electro-optic, or EO, effect. Devices that include materials that change their refractive index in response to changes in an applied electric potential are called electro-optical (EO) devices.

The second-order hyperpolarizability ($\gamma$) or third-order susceptibility ($\chi^{(3)}$), are the normal measures of third-order NLO activity. While there are several methods used to measure these properties, degenerate four-wave mixing (DFWM) is very common. See C. W. Thiel, "For-wave Mixing and Its Applications," www.physics.montana.edu/students.thiels.docs/FWMixing.pdf, the entire contents of which are hereby incorporated herein by reference. Referring to Published U.S. Patent Application No. US 2012/0267583A1, the entire contents of which are incorporated herein by reference, a method of evaluating third-order NLO properties of thin films, known in the art as Degenerate Four Wave Mixing (DFWM), can be used. In FIG. 4 of US 2012/0267583A1, Beams 1 and 2 are picosecond, coherent pulses, absorbed by the NLO film deposited on a glass substrate. Beam 3 is a weaker, slightly delayed beam at the same wavelength as Beams 1 and 2. Beam 4 is the resulting product of the wave mixing, diffracted off of the transient holographic grating, produced by interferences of beams 1 and 2 in the NLO material of the film. Beam 3 can be a "control" beam at a telecom wavelength which produces a "signal" beam at a frequency not absorbed by the NLO material.

Suitable electron-accepting groups "A" (also referred to in the literature as electron-withdrawing groups) for nonlinear optical chromophores in accordance with the various embodiments of the present invention include those described in published U.S. Patent Applications: US 2007/0260062; US 2007/0260063; US 2008/0009620; US 2008/0139812; US 2009/0005561; US 2012/0267583A1 (collectively referred to as "the prior publications"), each of which is incorporated herein by reference in its entirety; and in U.S. Pat. Nos. 6,584,266; 6,393,190; 6,448,416; 6,44,830; 6,514,434; 5,044,725; 4,795,664; 5,247,042; 5,196,509; 4,810,338; 4,936,645; 4,767,169; 5,326,661; 5,187,234; 5,170,461; 5,133,037; 5,106,211; and 5,006,285; each of which is also incorporated herein by reference in its entirety.

In various nonlinear optical chromophores in accordance with various preferred embodiments of the present invention, suitable electron-accepting groups include those according to general formula (I$^a$):

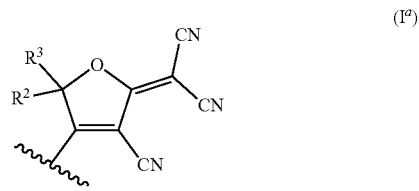

wherein $R^2$ and $R^3$ each independently represents a moiety selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocyclic, substituted or unsubstituted heterocyclic, substituted or unsubstituted cyclohexyl, and $(CH_2)_n$—O—$(CH_2)_n$ where n is 1-10. In various particularly preferred embodiments, the electron-accepting group is

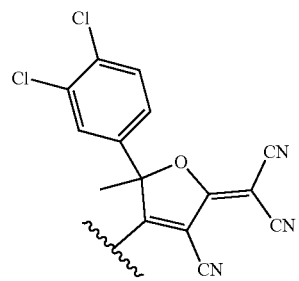 [SMILES: *C1=C(C#N)C(=C(C#N)C#N)OC1(C)c1ccc(Cl)c(Cl)c1]

Suitable electron-donating groups "D" for nonlinear optical chromophores in accordance with the various embodiments of the present invention include those described in published U.S. Patent Applications: US 2007/0260062; US 2007/0260063; US 2008/0009620; US 2008/0139812; US 2009/0005561; US 2012/0267583A1 (collectively referred to as "the prior publications"), each of which is incorporated herein by reference in its entirety; and in U.S. Pat. Nos. 6,584,266; 6,393,190; 6,448,416; 6,44,830; 6,514,434; 5,044,725; 4,795,664; 5,247,042; 5,196,509; 4,810,338; 4,936,645; 4,767,169; 5,326,661; 5,187,234; 5,170,461; 5,133,037; 5,106,211; and 5,006,285; each of which is also incorporated herein by reference in its entirety.

Nonlinear optic chromophores according to the present invention can further comprise one or more pendant spacer groups bound to the core, first bridging group, second bridging group, electron donating group and/or electron accepting group. Pendant spacer groups in accordance with the present invention are generally nonreactive moieties which extend outward from the chromophore and create steric hindrance (i.e., "spacing") between two or more of the chromophore molecules in a material containing the chromophores, and thus serve to prevent aggregation during and after poling.

In various embodiments wherein a or b in general formula (I) is 1, that carbon-carbon double bond in the formula can be replaced with a carbon-carbon triple bond.

Suitable bridging groups (B) for nonlinear optical chromophores according to general formula (II) of the present invention include those described in U.S. Pat. Nos. 6,584,266; 6,393,190; 6,448,416; 6,44,830; 6,514,434; each of which is also incorporated herein by reference in its entirety. Alternatively, in various preferred embodiments, bridging groups (B) for nonlinear optical chromophores according to general formula (II) of the present invention include those of the general formula (II$^b$):

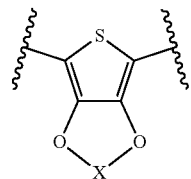

(II$^b$)

wherein X represents a substituted or unsubstituted, branched or unbranched $C_2$-$C_4$ diyl moiety.

Nonlinear optical chromophores in accordance with the various embodiments of the present invention exhibit significantly improved properties over prior art chromophores. Nonlinear optical chromophores in accordance with the various embodiments of the present invention exhibit significantly improved $r_{33}$ values. Additionally, nonlinear optical chromophores in accordance with the various embodiments of the present invention exhibit greater stability in a variety of polymer matrix materials. Optical properties and stability of nonlinear optical chromophores in accordance with the various embodiments of the present invention can be measured, for example, as described in US 2012/0267583A1.

Nonlinear optical chromophores in accordance with the various embodiments of the present invention can be synthesized using commercially available reagents and reactions, as described below. For example, 3,4-ethylenedioxythiophene and (4-(diethylamino)phenyl)methanol can each be obtained commercially from Sigma-Aldrich, or synthesized by methods known in the art.

In a first preliminary step, a phosphonium salt ylide of an electron-donating group is formed. For example, an electron-donating group precursor, such as (4-(diethylamino)phenyl)methanol, can be reacted with triphenylphosphine in the presence of acetic acid and hyrdobromic or hydroiodic acid in a solvent such as dichloromethane to form N,N-diethylaniline-4-methylenephosphonium bromide or iodide.

In a second preliminary step, an aldehyde of a thiophene bridging group is formed. For example, a thiophene bridging group, such as 3,4-ethylenedioxythiophene, is reacted with dimethylformamide in the presence of phosphoryl chloride to form 3,4-ethylenedioxythiophene-2-aldehyde.

Next, using a Wittig reaction, the thiophene bridging group aldehyde derivative can be reacted with the phosphonium salt ylide to form an alkene adduct thereof. For example, 3,4-ethylenedioxythiophene-2-aldehyde can be reacted with N,N-diethylaniline-4-methylenephosphonium bromide the resulting alkene (A):

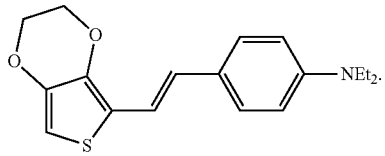

(A)

The alkene adduct (A) can then be reacted with n-butyl lithium in tetrahydrofuran, followed by reaction with an acrolein such as 3-(N,N-dimethylamino)acrolein to form intermediate (B):

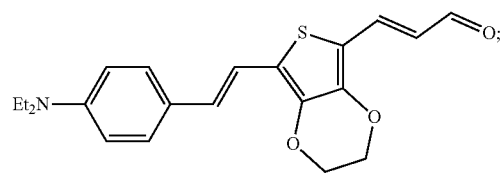

(B)

or alternatively reacted with dimethylformamide in the presence of phosphoryl chloride to form intermediate (C):

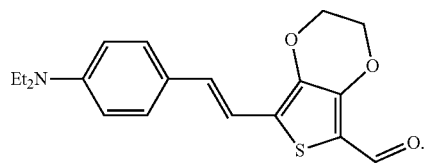

(C)

The thiophene bridging group/electron-donating group adduct aldehyde, e.g., intermediate (B) or intermediate (C), can then be reacted with an electron-accepting group, for example, via a Knoevenagel reaction, to replace the aldehyde with a carbon-carbon double bond linking the adduct to the electron accepting group.

The present invention also includes nonlinear optical materials comprising a nonlinear optic chromophore according to an embodiment of the invention incorporated within a matrix material. Suitable matrix materials can include polymers, such as, for example: poly(methylmethacrylate)s (PMMA); polyimides; polyamic acid; polystyrenes; poly(urethane)s (PU); and amorphous polycarbonates (APC). In various preferred embodiments the matrix material comprises a poly(methylmethacrylate). Particularly preferred poly(methylmethacrylate)s have a molecular weight of about 120,000 and a glass transition temperature Tg of about 85-165° C.

The nonlinear optic chromophore according to an embodiment of the invention is generally incorporated within the matrix material at a loading of 1% to 50% by weight, based on the entire nonlinear optical material, more preferably at a loading of 2% to 35% by weight, and most preferably at a loading of 3% to 35% by weight. Nonlinear optical materials in accordance with various embodiments of the invention can be in the form of solid thin films, optionally disposed on a surface of another material. In general, nonlinear optical materials according to the present invention include all existing known forms of such materials, but wherein the optical chromophore incorporated within the matrix material comprises a nonlinear optic chromophore according to an embodiment of the invention described herein.

The present invention also relates to electro-optic devices comprising a nonlinear optical material according to various embodiments of the present invention. Electro-optic device and/or system embodiments of the present invention include phased array radar, satellite and fiber telecommunications, cable television (CATV), optical gyroscopes for application in aerial and missile guidance, electronic counter measure systems (ECM) systems, backplane interconnects for high-speed computation, ultrafast analog-to-digital conversion, land mine detection, radio frequency photonics, spatial light modulation and all-optical (light-switching-light) signal processing, wherein such devices include a nonlinear optical material according to the present invention. Moreover, the extremely broad absorption spectrum of nonlinear optic chromophores according to the present invention, which essentially covers the entire UV-visible-near infrared region from 250 nm to 1800 nm at high extinction coefficient, indicates that nonlinear optical materials according to various embodiments of the present invention can also be used in solar conversion and photovoltaic devices.

One preferred electro-optic device embodiment according to the present invention includes electro-optic modulators for telecommunications, wherein the modulator comprises a nonlinear optical material according to the present invention. Another preferred device is an all-optical device. Such a device can be used for optical switching, parametric amplification and other all-optical applications of the third-order hyperpolarizability.

The invention will now be described in further detail with reference to the following non-limiting example.

EXAMPLES

Example 1: Synthesis of a Non-Linear Optical Chromophore in Accordance with an Embodiment of the Invention Step 1): A round bottom flask was charged with N,N-diethylaniline (29.8 mL), triphenylphosphine (29.8 g), potassium iodide (31.2 g), chloroform (940 mL), acetic acid (37.6 mL) and formaldehyde (37% aqueous, 36.6 mL). The reaction was stirred at 50° C. for 60 hours under nitrogen. After cooling, the phases were separated, the organic portion was evaporated and the residue crystallized from ethanol providing N,N-diethylaniline-4-methylenephosphomiun iodide in 74% yield, 92% pure.

Step 2): A round bottom flask was charged with dichloromethane (600 mL), N,N-dimethylformamide (10.4 mL) and phosphoryl chloride (12.6 mL). The reaction was stirred under $N_2$ for 1 hour. 3,4-ethylenedioxythiophene (17.5 g) was added and stirring continued for 24 hours. Aqueous sodium hydroxide (1N, 100 mL) was added and the reaction was stirred overnight. The phases were separated, dichloromethane dried with magnesium sulfate and evaporated. The resulting solid was dissolved in hot ethyl acetate, set aside to cool then filtered providing 3,4-ethylenedioxythiophene-2-aldehyde as yellow needles, 27.7 g, 98% yield, 98% pure.

Step 3): A round bottom flask was charged with 3,4-ethylenedioxythiophene-2-aldehyde (8.91 g), N,N-diethylaniline-4-methylenephosphomiun iodide (27.9 g), dichloromethane (255 mL) and sodium hydroxide (50% aqueous, 51 mL). The reaction was vigorously stirred overnight. The phases where separated, the dichloromethane solution was dried with magnesium sulfate then evaporated giving a honey colored syrup. The syrup crystallized upon setting. The mixture was triturated in ether and filtered removing 85% of the triphenylphosphine oxide. The filtrate was evaporated and the residue chromatographed on silica gel eluting with hexane/ethyl acetate (3:1). The appropriate fractions were combined and evaporated giving (E)-4-(2-(2,3-dihydrothieno[3,4-b][1,4]dioxin-5-yl)vinyl)-N,Ndiethyl-benzenamine as a thick yellow syrup which crystalized upon setting, 14.1 g, 95% yield, 96% pure.

Step 4): (E)-3-(7-((E)-4-(diethylamino)styryl)-2,3-dihydrothieno[3,4-b][1,4]dioxin-5-yl)acrylaldehyde: A round bottom flask was charged with (E)-4-(2-(2,3-dihydrothieno [3,4-b][1,4]dioxin-5-yl)vinyl)-N,Ndiethylbenzenamine (2.28 g) and THF (20 mL). The mixture was chilled to −70° C. then n-Butyl lithium(2.5N in hexane, 3.5 mL) was added and the reaction was stirred at 0° C. for 30 minutes. The 3-(N,Ndimethylamino) acrolein (1.0 mL) was added and the reaction was stirred another 30 minutes at 0° C. The still cold reaction was quenched with water, diluted with ethyl acetate, washed with brine, dried with magnesium sulfate and evaporated. The residue was chromatographed with ethyl acetate/hexane(1:3-1:2). The appropriate fractions were combined and evaporated giving (E)-3-(7-((E)-4-(diethylamino) styryl)-2,3-dihydrothieno[3,4-b][1,4]dioxin-5-yl)acrylaldehyde as a red powder, 2.10 g, 74% yield, cis to trans ratio 1:9, 91% pure.

Step 5): 3-(3,4-dichlorophenyl)-3-hydroxybutan-2-one: A dried round bottom flask was evacuated and filled with nitrogen three times then charged with 2,3-butanedione (4.38 mL) and tetrahydrofuran (250 mL). While under nitrogen the solution was chilled to 0° C. then 3,4-dichlorophenylmagnesium bromide (0.5 N in tetrahydrofuran, 50 mL) was added in a steady stream by cannula using nitrogen pressure. The ice bath was removed and the reaction was stirred under nitrogen for 1 hour. The reaction was quenched with saturated ammonium chloride, diluted with ethyl acetate, washed with water then brine, dried with magnesium sulfate and evaporated giving 3-(3,4-dichlorophenyl)-3-hydroxybutan-2-one as a thick syrup. The crude product was used without purification.

Step 6): A dry round bottom flask was charged with 3-(3,4-dichlorophenyl)-3-hydroxybutan-2-one (5.80 g), malononitrile (3.30 g) then the flask was evacuated and charged with nitrogen three times. Anhydrous ethanol (65 mL) was added then lithium ethoxide (1N in ethanol, 2.5 mL) was added. A Soxhlet extractor, with a thimble filled with molecular sieves, was added and the reaction was refluxed under nitrogen overnight. After 24 hours the reaction was allowed to cool, neutralized with 1N hydrochloric acid to a pH of ~6,diluted with ethyl acetate, washed with water then brine, dried with magnesium sulfate and evaporated giving a thick past. Chromatography (silica gel, CHC13) gave a light yellow powder. The powder was refluxed in ethanol, allowed to cool, filtered, washed with ethanol and dried giving 3-cyano-2-(dicyanomethylene)-4,5-dimethyl-5-(3,4-dichlorophenyl)-2,5-dihydrofuran as a yellow powder, 4.80 g, 52% yield (for two steps, 5 & 6), 94% pure.

Step 7): A round bottom flask was charged with (E)-3-(7-((E) (diethylamino)styryl)-2,3-dihydrothieno[3,4-b][1,4] dioxin-5-yl)acrylaldehyde (3.43 g), 3-Cyano-2-(dicyanomethylene)-4,5-dimethyl-5-(3,4-dichlorophenyl)-2,5-dihydrofuran (3.62 g), tetrahydrofuran (40 mL), ethanol (10 mL) and piperidine (0.2 mL). The reaction was stirred at 80° C. for 24 hours. The reaction was evaporated. The residue was chromatographed on silica gel eluting with dichloromethane. The appropriate fractions were combined and evaporated. The residue was re-chromatographed on silica gel eluting with hexane/ethyl acetate. The cleanest fractions were combined and evaporated. The residue was dissolved in dichloromethane and crystallized by evaporation. The crystals were soaked in ether overnight. The ether was decanted off and fresh ether added, daily, for four more days. Fresh ether was added, again, followed by trituration, filtration, wash with ether and drying gave 3-cyano-2-(dicyanomethylene)-4-((1E,3E)-4-(7-((E)-4-(diethylamino) styryl)-2,3-dihydrothieno[3,4-b][1,4]dioxin-5-yl)buta-1,3-dienyl))-5-methyl-5-(3,4-dichlorophenyl)-2,5-dihydrofuran (I″) as very fine copper colored crystals, 1.44 g, 22% yield, 100% trans, 99% pure.

(I″)

Example 2: Evaluation of Optical Properties

The $r_{33}$ value of nonlinear optical chromophore (I″) prepared in Example 1 was measured at 1310 nm wavelength (25% loading in APC) to be 105 pm/V. This is significantly better than the $r_{33}$ values reported in the literature for various prior art chromophores containing similar electron-accepting groups and/or similar electron-donating groups. Thus, the improved properties are attributable to the novel and improved donor-bridge-acceptor combinations in accordance with the various embodiments of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A nonlinear optical chromophore of the general formula (I″)

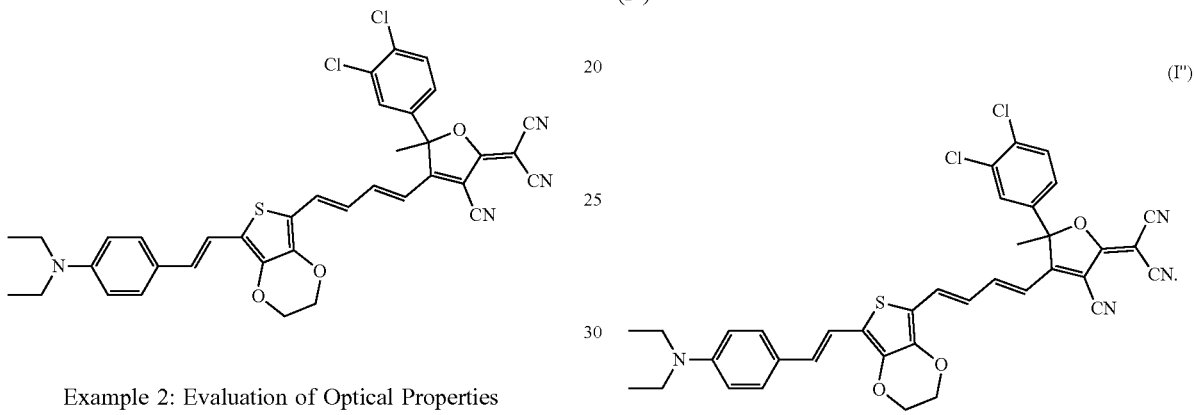

* * * * *